United States Patent [19]

Zanetti et al.

[11] Patent Number: 4,989,611
[45] Date of Patent: Feb. 5, 1991

[54] CARDIAC COMPRESSION WAVE MEASURING SYSTEM AND METHOD

[75] Inventors: John M. Zanetti, Long Lake; David M. Salerno, Minneapolis, both of Minn.

[73] Assignee: SeisMed Instruments, Inc., Minneapolis, Minn.

[21] Appl. No.: 234,031

[22] Filed: Aug. 19, 1988

[51] Int. Cl.$^5$ .............................................. A61B 5/02
[52] U.S. Cl. ....................................... 128/695; 128/687
[58] Field of Search ............... 128/668, 695, 696, 687, 128/714–715

[56] References Cited

U.S. PATENT DOCUMENTS

| Re. 27,042 | 1/1971 | Jorgensen et al. |
| Re. 31,097 | 12/1982 | Vas et al. |
| 3,318,303 | 5/1967 | Hammacher |
| 3,385,289 | 5/1968 | Lawson et al. |
| 3,695,253 | 10/1972 | Vielhauer ............................. 128/695 |
| 3,762,397 | 10/1973 | Cage |
| 3,773,033 | 11/1973 | Rodbard et al. |
| 3,878,832 | 4/1975 | Tickner et al. |
| 3,908,639 | 9/1975 | McIntyre ......................... 128/695 X |
| 4,094,308 | 6/1978 | Cormier |
| 4,204,544 | 5/1980 | Feldstein et al. |
| 4,362,164 | 12/1982 | Little et al. |
| 4,378,022 | 3/1983 | Suobank et al. .................... 128/715 |
| 4,378,022 | 3/1983 | Suobank et al. |
| 4,383,534 | 5/1983 | Peters |
| 4,422,458 | 12/1983 | Kravath |
| 4,428,380 | 1/1984 | Wong et al. |
| 4,446,873 | 5/1984 | Groch et al. |

FOREIGN PATENT DOCUMENTS 0264329 4/1988 European Pat. Off.
2316130 10/1947 Fed. Rep. of Germany.
86/04802 8/1988 PCT Int'l Appl.

OTHER PUBLICATIONS

Showalter, S. J. et al., "A Quantitative Description of the Aortic Ejection Click and First Heart Sound", 3rd Ann. Symp. on Comp. Appln. in Med., 10/14–10/17/1979, Wash. D.C.
Moyer, D. F. et al., "Instrumentation for the Diagnosis of CAD", A IEEE Transactions, vol. 80, part 1, 1961, pp. 717–721.
Iwata, A. et al., "Algorithm for Detecting the First & Second Heart Sounds by Spectral Tracking", Med. & Biol. Eng. & Computing, Jan. 1980, pp. 19–26.
Nandagopal, D. et al., "Spectral Analysis of Second Heart Sound in Normal Children by Selective LPC", MBEC, May 1984, p. 229.
Sarkady, A. et al., "A 16-Bit Micro-Computer Based Biomedical Signal Processor", 3rd Annual Symp. on Computer Applns. in Medicine, Oct. 14–17, 1979, Wash., D.C.
Copy of p. 402 of *McGrow-Hill Dictionary of Scientific and Technical Terms*, Fourth Edition, containing the definition of "Compressional Wave".
Copy of a Manufacturer's Brochure Page Showing the PCT Model 393C Seismic Accelerometer.
Copy of the Operator's Manual for the Cardiokinetic Cardiokymograph.
IEEE Transactions on Biomedical Engineering, vol. BME-26, No. 1, Jan. 1979, D. H. Zilm et al.
Electronic Design, vol. 26, No. 4, Feb. 15, 1978, "IC Accelerometer—So Tiny, It Monitors the Heart from Within".

*Primary Examiner*—Francis Jaworski
*Attorney, Agent, or Firm*—Merchant, Gould, Smith, Edell, Welter & Schmidt

[57] ABSTRACT

Seismic techniques and principles are used to provide a noninvasive method and apparatus for assessing selective cardiac performance by detecting compression waves generated by heart muscle function. An analog signal is generated by detecting compression waves in the range of 0.025 Hz to about 800 Hz at an exterior surface of a subject's body by an accelerometer having a sensitivity of one (1) micro inch at one (1) Hz. Compression waves at frequencies above about 50 Hz are eliminated from the analog signal and then single full-cycle functions of the heart muscle are selected from a series of such cycles making up the analog signal. The selected single cycles may be averaged and waveform distortion may be removed from the averaged signal. Total energy level of the compression wave may be calculated and then the averaged signal may be displayed for visual analysis of a compression wave cycle representative of the muscle function of the heart.

4 Claims, 5 Drawing Sheets

CARDIAC COMPRESSION WAVE MEASURING SYSTEM AND METHOD

BACKGROUND OF THE INVENTION

The invention relates to a method and apparatus for noninvasive assessment of cardiac performance by detection of compression waves generated by heart muscle function. The method and apparatus involves the detection of cardiovascular abnormalities for monitoring the function of the heart muscle by detecting at the exterior surface of the body, compression waves generated by heart muscle function.

Coronary artery disease is one of the leading causes of death and disability in the United States. Currently, there are an estimated six million individuals in the United States who have symptomatic coronary artery disease. Undoubtedly, there are many more with the disease who have not yet felt the symptoms of the disease due to its particular characteristics. Some authorities have estimated that about half of those affected with the disease are in apparently good physical health and are totally unaware of the presence of the disease. In 1985 an estimated 540,000 deaths occurred due to coronary artery disease and more than 700,000 patients in the United States were hospitalized with acute myocardial infarction. Accordingly, researchers and physicians who specialize in this area are constantly striving to develop simple and safe methods for early detection of the diseases of the heart. The objective is to develop methods and apparatus which are cost-effective so that they can be used on a routine basis.

Because of the potentially large number of apparently healthy people who have various stages of cardiovascular disease, a number of attempts at detecting the disease have been tried. Currently, there are several methods used for testing for myocardial ischemia. One such test is coronary angiography. This test is a reliable method for detecting narrowing of coronary arteries. This invasive procedure requires the insertion of catheters into or near the heart. Because of the invasive nature of this test, it involves risk of medical complications. Occasional fatalities will result from the procedure. Because of the risks of using this method and because of the cost attendant to use of the technique, physicians and researchers are constantly attempting to develop a variety of noninvasive techniques which can achieve reliability in providing accurate information concerning the extent and nature of cardiovascular disease.

The most widely used technique for noninvasive screening of patients for coronary artery disease involves electrocardiography. This noninvasive method and the apparatus utilized for conducting the tests detects the bioelectric potential of the heart muscle and provides a graphic display of the bioelectrical activity in the muscle for analysis by the physician. The display may be used for later comparison with additional electrocardiograms.

Exercise electrocardiography (ECG) is frequently used in a technique which involves making two or more records of the patient's heart muscle electrical function. In this technique, the individual's "at rest" cardiovascular function is first recorded. Then the patient undergoes a period of controlled strenuous exercise. During the course of this controlled strenuous exercise, additional electrocardiograms are prepared for comparison to the ECG which has been recorded at the patient's "at rest" condition. The comparison is made on the theory that strenuous exercise will produce a transient imbalance in the patient's heart oxygen supply. It is believed that this transient imbalance occurs between the heart's oxygen requirements and the oxygen which is supplied by the blood flow in the coronary artery. It is believed that this oxygen imbalance will be imposed by the strenuous exercise. Such an imbalance may be detected by the development of electrocardiographic abnormalities which are believed typical of coronary artery disease.

Unfortunately, it has been learned that the electrocardiographic technique seems to be relatively insensitive to the oxygen imbalance that apparently occurs, and therefore, the reliability of this technique is not as high as might be desired. Some authorities have placed the probability of successful diagnosis using this technique at only about sixty percent (60%) in patients with symptoms suggestive of coronary artery disease. Further, it has been found that as many as half of the patients who exhibit abnormal ECG readings during the strenuous exercise portion of the test, but who are otherwise healthy, do not actually have coronary arterial disease. Therefore, while exercise electrocardiography provides a relatively safe, noninvasive technique which is relatively low in cost, it, nevertheless, provides a procedure which does not have the accuracy desired by the medical profession.

Other examples of alternate procedures to coronary angiography are such noninvasive techniques as exercise radionuclide ventriculography, exercise thallium-201 testing and exercise echocardiography.

Exercise radionuclide ventriculography (MUGA) is a procedure of noninvasive testing which requires the injection of radioactive materials. Myocardial function deteriorates rapidly when ischemia develops. In animal models, a heart wall motion abnormality develops in the heart muscle within seconds of coronary artery occlusion in that part of the myocardium perfused by the occluded artery. Exercise radionuclide ventriculography takes advantage of this condition. The test is done by radioactive labeling of the patient's red blood cells, so that scans of the heart show the internal shape and amount of contraction. Images obtained before exercise can then be compared to exercise and post-exercise scans. This procedure is expensive and time consuming. While the sensitivity of this method is relatively good, its specificity, and, therefore, its predictive accuracy is somewhat less than desired.

Another method of noninvasive testing involves the use of thallium-201, which is a radioactive material that can detect blood flow abnormalities to the heart during myocardial ischemia. Thallium-201 is an analogue of potassium, the major intracellular cation of the heart muscle. The thallium therefore quickly enters functioning heart muscle cells, but does not enter ischemic cells. When injected during exercise, the thallium image will show poor uptake in areas of ischemia. This test also is time consuming as well as relatively costly. The method requires the injection of radioactive material and, for this and other reasons, physicians continue to desire less stressful and less time consuming methods of examining and testing patients.

A third technique, exercise echocardiography, attempts to visualize cardiac wall motion abnormalities induced by ischemia by obtaining ultrasound images of the heart before, during and after exercise. A handheld probe applied to the chest wall transmits and receives ultrasonic waves directed at the heart. Problems with the o technique include the need for considerable expertise in obtaining the images, frequent failure to obtain adequate images during exercise because of motion artifact and high equipment costs.

As mentioned above, tests on animal subjects have shown that reduction in blood supply to the heart muscle can be detected by studying the movements of segments of the heart wall. These studies have revealed that when segments of the heart muscle receive less oxygen than required for proper function, the normal contraction pattern of the heart muscle will change. The change in heart muscle function occurs because of the lack of oxygen supplied to the muscle through the coronary arteries. It is these abnormalities in the function of the heart muscle itself which are of concern to the physician. Other methods of noninvasive detection of heart muscle function have limitations which are troublesome when the methods are used for screening patients. Methods using the electrical field (e.g. electrocardiography) effect around muscle tissue are presented with problems of shielding the environment in which the patient is being tested from extraneous electrical fields. Testing the muscle function of the heart by measuring the electrical field at or in the heart area requires detecting changes in the electrical field that are extremely small. These small changes in the electrical field can be affected by other diagnostic or electrical equipment which is frequently operated in the immediate area of the testing site.

Similar problems can occur when testing systems rely on changes in the electromagnetic field surrounding the heart (e.g. cardiokymography). Detection of changes in the electromagnetic field in or surrounding the heart also requires detection of extremely small changes in an electromagnetic field. Again, the detection of relative weak magnetic fields can be dramatically affected by equipment operated in the same room or in the proximity of the test site. These uncontrolled fields, of course, present a serious problem for these testing methods since they can obscure or destroy the data which is collected.

The present invention avoids the use of extremely weak electric and electromagnetic fields and relies on wave energy of the type analogous to seismic waves generated in the crust of the earth as a result of earthquake activity. The functioning of the heart muscle generates compression waves which are transmitted throughout the body just as seismic waves travel throughout the earth when an earthquake occurs. In the case of the human heart, the natural muscle function involved with the contraction and relaxation of the muscles of the heart generate compression waves which have been found to travel throughout the body of the patient.

Experimental investigation has revealed that the nature of these compression waves generated by the heartbeat infer detailed characteristics of the specific muscle function of the heart and can be relied on for detecting abnormal muscle function. As previously indicated, when oxygen supply to the muscle of the heart is interrupted, the muscle reacts accordingly. The muscle may cease contractions or may produce contractions that are weak or in some way altered by the lack or reduction of oxygen supply to the muscle. These abnormal muscle contractions or function produce compression waves which are indicative of the abnormal muscle function. Detection of this abnormal muscle function then can indicate the presence of coronary arterial disease in a noninvasive fashion so that proper treatment can be applied to the disease.

The present invention provides an effective method of noninvasive testing and screening patients for coronary arterial disease since the detection of the compression waves generated by heart can be detected at the outer surface of the body. The procedure does not require injection of radioactive substances, chemicals, or catheters for treatment. It can be administered quickly by properly trained medical personnel. Further, it provides for a graphic record for comparison with normals and for baseline recording to compare to future recordings in the same individual, and for future analysis or comparison with further such tests.

OBJECT OF THE INVENTION

It is, therefore, an object of the present invention to provide a method and apparatus for detecting body tissue movement utilizing measurement of compression waves generated by heart muscle function.

Another object of the present invention is to provide a method and apparatus for detecting muscle function of the heart by detecting compression waves generated by heart muscle function transmitted to the outer wall of the chest cavity of a living body.

Another object of the present invention is to provide a method and apparatus for noninvasive detection of abnormal muscle function of the heart by detecting compression waves generated by heart muscles through the use of a detector placed on the outer surface of the body.

A further object of the present invention is to provide a method and apparatus for detecting compression waves in the frequency range of about 0.025 Hz to about 800 Hz generated by heart muscle function.

An object of the present invention is to provide an apparatus for detecting compression waves in the frequency range of about 0.025 Hz to about 800 Hz generated by heart muscle function using an accelerometer capable of detecting movement of about one (1) microinch at a frequency of about one (1) Hz.

A further object of the present invention includes a method and apparatus for noninvasively assessing heart muscle function by detecting compression waves generated by the heart muscle at the surface of the patient's body by applying a transducer to the outside surface of the body at predetermined locations to detect compression waves in the frequency range of about 0.25 Hz to about 800 Hz and selection of compression waves within the frequency range of about 0.025 Hz to about 50 Hz to assess the function of the heart muscle.

Another object of the invention is to provide a method and apparatus for assessing cardiac performance by generating a signal indicative of compression waves generated by heart muscle function by applying a piezoelectric transducer to the outside surface of the body to detect compression waves in the frequency range of about 0.025 Hz to about 800 Hz and eliminating those compression wave frequencies above 50 Hz after which the generated signal is conditioned and displayed for analysis of the wall muscle function of the heart.

A further object of the present invention is to provide a noninvasive method and apparatus for assessing cardiac performance by applying a transducer capable of detecting heart muscle generated compression waves in the frequency range of about 0.025 Hz to about 800 Hz to detect the muscle function of the heart to provide a signal for display and analysis of the wall muscle function of the heart.

Where the words "patient," "subject," or "body," are used, the words are intended to include both humans and animals. The methods and apparatus of this invention can be used with equal success on humans and a wide range of other animals such as the common household pets.

SUMMARY OF THE INVENTION

The present invention relates to a method and an apparatus generally designated as a "seismocardiography ®." The seismocardiograph ® utilizes a transducer having a usable frequency response in the range of about 0.025 Hz to about 800 Hz for detecting compression waves generated by heart muscle function. Accelerometers of various types may be used to illustrate the features of the invention. The accelerometer may use strain gauge type transducers, piezoelectric type or others, provided the transducers provide the sensitivity necessary to the function of the apparatus. An example of a strain gauge transducer is produced by PCB Piezotronic, Inc. Piezoelectric crystal may also be used in an accelerometer with success. Other types of transducers may be used, provided the transducer has at least a sensitivity to movement of one (1) microinch at a frequency of one (1) Hz. A preferred embodiment of this invention utilizes a piezoelectric crystal and therefore the invention will be described with reference to such a transducer. A commercially available transducer suitable for practicing this is available from PCB Piezotronics as the Model 393C Seismic Accelerometer. A piezoelectric crystal is selected which has a usable response in the frequency range of about 0.025 Hz to about 800 Hz for detecting compression waves normal to the outside surface of the human body where the transducer is placed for detection of the compression waves generated by heart wall muscle function.

The full-cycle functioning of the heart wall muscle is detected by detection of heart muscle-generated compression waves using a piezoelectric transducer. The transducer generates an analog signal in which frequencies of the compression waves above about 50 Hz are eliminated. The resulting analog signal is a band limited signal which can then be converted to a digital signal for further processing and analysis. Selected single-cycle portions of the converted digital signal may be selected and averaged to provide an averaged compression signal representing a full cycle of the patient's heartbeat. The averaged signal may then be conditioned to remove amplitude distortions at the beginning and the end of each of the averaged single-cycle portions.

The signal representing single-cycle function of the heart wall muscles is then input to a Fourier transform algorithm where the signal is separated into discrete frequency components after which total energy level calculations are made of the discrete frequency components to provide an energy output signal. The averaged signal and the energy output signal are then visually displayed on a display device such as a graphic recorder or a video monitor. The displayed signal provides an opportunity for visual analysis of the compression wave characteristics of the heart muscle function. This visual display provides a physician with a means for analyzing unusual muscle function of the heart. The averaged signal and the energy output signal are also stored on magnetic media.

In one version of the invention, an electrocardiographic signal is simultaneously generated along with generation of the analog signal from detection of the compression wave by the piezoelectric crystal. The electrocardiogram provides a marker signal of known characteristics which can then be utilized as a reference signal for comparison to the analog signal generated by the compression waves. The electrocardiographic reference signal is only one example of the type of marker signal which might be used. Other examples of marker signals that might be used are those signals generated by blood pressure reading and by phonocardiogram. The important feature is that the reference signal of the electrical field activity of the heart can be simultaneously recorded with the detection of the compression wave generated by the heart wall muscle. The simultaneously generated electrocardiographic signal which can be used for timing purposes used to compare to the finally displayed compression wave signal in order to more accurately detect either normal or unusual muscle function of the heart when the muscle is subjected to loss of oxygen through occlusions in the coronary arteries or through some other malfunction of the heart which induces abnormal heart muscle activity.

Other aspects and advantages of the present invention will become apparent from the following, more detailed description considered in conjunction with the accompanying drawings.

DETAILED DESCRIPTION OF THE INVENTION

Figure 1:
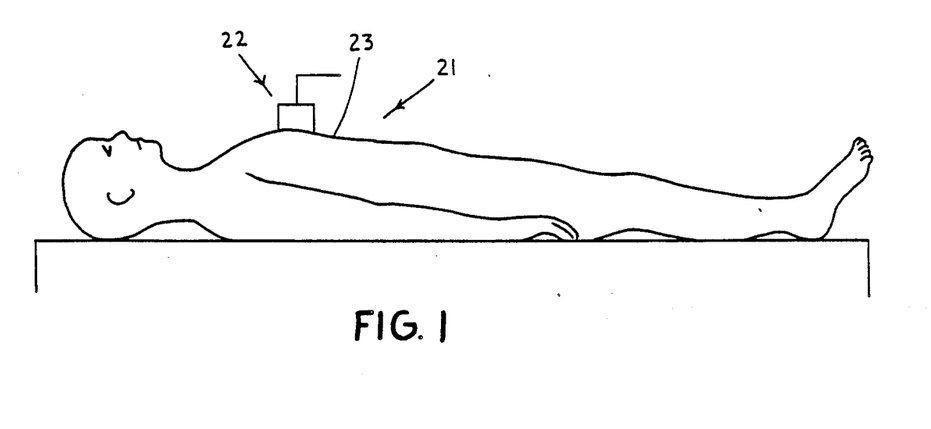
FIG. 1 illustrates a transducer applied to the chest region of a horizontally disposed patient.
Figure 2:
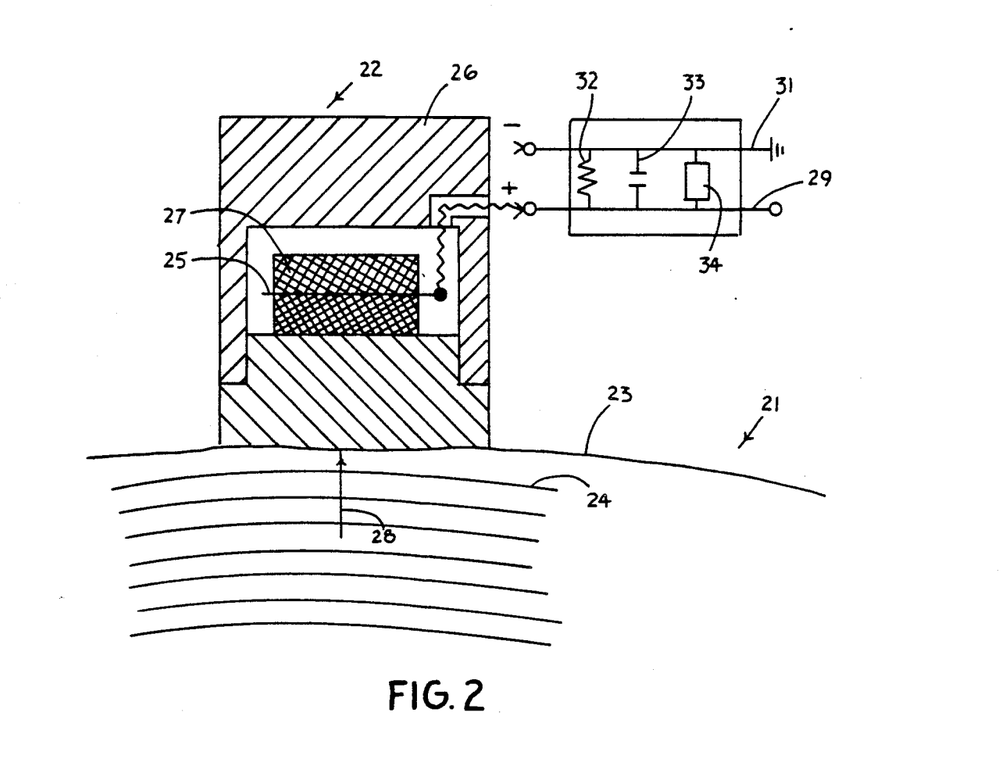
FIG. 2 is a cross-sectional view of a transducer illustrating a piezoelectric crystal positioned in the transducer according to the present invention.

FIGS. 1 and 2 of the drawings illustrate an important feature of the invention. In FIG. 1 of the drawings, a subject 21 is illustrated in a horizontal position with a transducer in the form of an accelerometer 22 positioned normal to an outside surface 23 of the subject body. Accelerometer 22 is designed to respond to compression waves of the type which are familiar in the field of seismology. As with the measurement of seismic waves in large bodies, it has been discovered that compression waves are generated in the tissues of the human body by muscle function. The rebound of blood against closed heart valves moves the heart. The contraction of the heart wall muscle moves the heart. The motion of the heart generates these compression waves. These compression waves travel through the body from the heart in the same way that seismic waves travel from the site of an earthquake in the earth's crust to the surface of the earth. In the case of the monitoring system contemplated by this invention, compression waves 24, illustrated in FIG. 2 of the drawings, are generated by the human heart and travel toward the surface of the body 23 through the tissues of the body. These compression waves 24 contain frequency components which are generated not only by the heart wall muscle but also those generated by other heart functions and by ambient noise.

The present invention takes advantage of the known frequency range of compression waves generated by operation of the muscle in the walls of the human heart and, particularly, those of the left ventricle by selecting an accelerometer 22 which is sensitive to the compression wave frequencies characteristic of the operation of the muscle of the left ventricle of the heart.

An important feature of such an accelerometer 22 is that it must be capable of detecting compression waves of ultralow frequency and which have a very low displacement amplitude. The accelerometer 22 must be sensitive to very small displacements caused by the compression waves generated in the heart muscle because the compression waves must travel substantial distances through body tissue before the waves reach the outside surface 23 of the human body where transducer accelerometer 22 is positioned for detecting the compression waves 24. It has been found that if the transducer is capable of detecting movement of at least one (1) microinch at a frequency of about one (1) Hz, then the transducer will satisfy the needs of this invention. To accommodate these high sensitivity requirements, the accelerometer 22 is constructed of a main body 26 which provides most of the mass for the accelerometer 22. The main body 26 is formed in two pieces. The majority of the mass is provided by upper portion 20. The lower portion 19 may rest directly on the patient 21. A piezoelectric crystal 27 in a preferred employment of the invention, is mounted within the accelerometer 22 and oriented so that the sensitive axis of the crystal 27 is parallel to the direction of waveform progression 28 of compression waves 24. In a typical orientation, the sensitive axis of the crystal 27 lies perpendicular to lead 25. As indicated, a strain gauge transducer will also work if it has the requisite sensitivity. As previously noted, a strain gauge type accelerometer of the type manufactured by PCB Pieziotronic, Inc., is typical of the known and state of the art strain gauge which will satisfy the operational criteria of the present invention. An acceptable alternate of a piezoelectric type of gauge can also involve a piezo-film which demonstrates piezoelectric characteristics and is sensitive to compressional waves. Such a film is polyvinylidine fluoride film manufactured by the Kynor Piezo Film Department of Penwalt Corporation located in Valley Forge, Penn. U.S.A. A detailed description of accelerometers using this film or the strain gauge are not set forth because the mode of operation and construction of such strain gauges are well known in the art. Other types of transducers might also be selected but the invention will be described using a piezoelectric crystal 27.

When the piezoelectric crystal 27 is positioned with respect to the surface 23 of the patient's body 21, compression wave 24 will displace the body surface 23 sufficiently to affect the crystalline structure of piezoelectric crystal 27. Piezoelectric crystal 27 is selected and positioned within the accelerometer 22 so that the crystalline sensitivity to movement responds to movement perpendicular or normal to the surface of the body 23. Compression wave movement 24 is also perpendicular to the body surface 23. Consequently, this movement caused by compression waves will be detected by the crystal 27.

When accelerometer 22 is positioned normal to the outside surface 23 of the patient 2 in the recumbent position, the compression wave 24 will alter the electrical charge of the piezoelectric crystal 27 as the compression wave slightly displaces the surface of the body 23 in a direction normal to surface 23. This slight normal displacement of the transducer 22 is sensed by the piezoelectric crystal 27 which generates a small change in electric current in response to the surface movement. The piezoelectric crystal 27 is sensitive enough to detect movements of surface 23 which are as low as one microinch at a frequency of 1 Hz. As previously indicated, this chest wall or surface 23 displacement is caused by the contraction and relaxation of the heart muscle which sets up the compressional wave 24. These compressional waves 24 move to the surface 23 through body tissue which includes bone and fluid.

Piezoelectric crystal 27 is also selected to have a usable response to compression waves in the frequency range from 0.025 Hz to about 800 Hz. Crystal 27 begins its response at about 0.025 Hz. With this range of frequency response, piezoelectric crystal 27 mounted in the accelerometer transducer body 26 provides an effective means of selecting those compression waves 24 having frequencies generated by contraction and relaxation of the muscles of the heart wall.

The transducer utilizing crystal 27 preferably has a linear frequency response in the frequency range from 0.025 Hz to about 800 Hz. Such a linear response eliminates the need for correcting or modifying the output signal. Depending on the type of transducer used, the response may not be linear for the entire indicated frequency range. In such a case, the response curve could be modified to make it appear linear and thus achieve the desired results. For example, some types of transducers may have a lower frequency response at the low end, 0.025 Hz, of the range. In such a case, the output response curve could be corrected or modified to make it appear linear over the entire range. This can be achieved through the use of well known electronic techniques using known components. In the preferred employment of the invention set forth herein, the piezoelectric crystal 27 selected does have a linear response for the full frequency spectrum from about 0.025 Hz to about 800 Hz.

Figure 3:
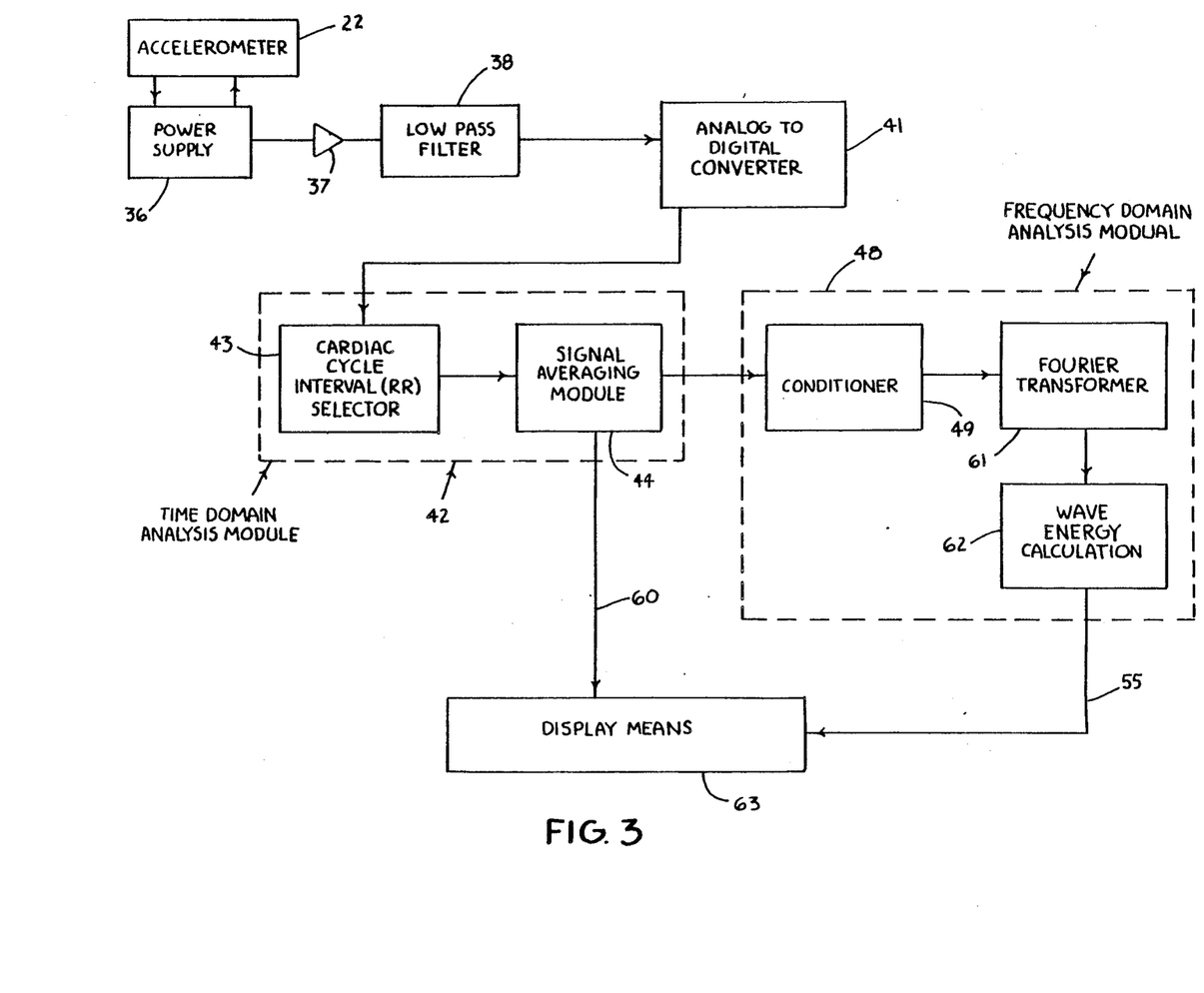
FIG. 3 is a block diagram of a first embodiment of the invention.

Power is applied to piezoelectric crystal 27 at lead 29. Ground 31 provides a ground for the accelerometer 22. Resistor 32 is an input resistor and capacitor 33 acts as an attenuating capacitor for the system. Amplifier 34 is provided to amplify the analog signal generated by the piezoelectric crystal 27. Power supply 36 (refer to FIG.

3 of the drawings) powers the built-in microelectronic amplifier 34 in the accelerometer 22. Amplifier 34 converts the high impedance charge variation from the piezoelectric crystal 27 to a low impedance voltage. This low impedance voltage is a signal which has been generated by the compression wave 24 emanating from function of the heart muscle. This low impedance signal is then isolated and amplified by isolation amplifier 37 to produce an amplified analog signal or analog compressional wave signal. This analog compression signal represents a series of cycles of the heartbeat.

Next, the amplified analog compressional wave signal from isolation amplifier 37 is filtered by low pass filter 38. Amplifier 37 amplifies all of the detected analog signal frequencies between 0.025 Hz to about 800 Hz. Low pass filter 38 removes all frequencies above about 50 Hz from the analog signal. The output from low pass filter 38 is therefore an analog signal having a frequency range of about 0.025 Hz to about 50 Hz. By eliminating all frequencies about 50 Hz from the detected compression wave 24, the analog signal output from low pass filter 38 then becomes a band limited output signal having only those frequencies in the range of about 0.025 Hz to about 50 Hz.

Studies have revealed that compression wave frequencies in the range of about 0.025 Hz to about 50 Hz are generated by heart muscle function of the walls of the heart. The objective of this invention is to evaluate heart muscle function in the wall of the heart particularly those in the left ventricle of the heart. This can be accomplished by using a filter 38 which is in effect a band pass filter designed to pass only the selected band of frequencies in the range of about 0.025 hz to about 50 Hz. Thus a band limited analog signal is generated as the output from filter 38.

Figure 6:
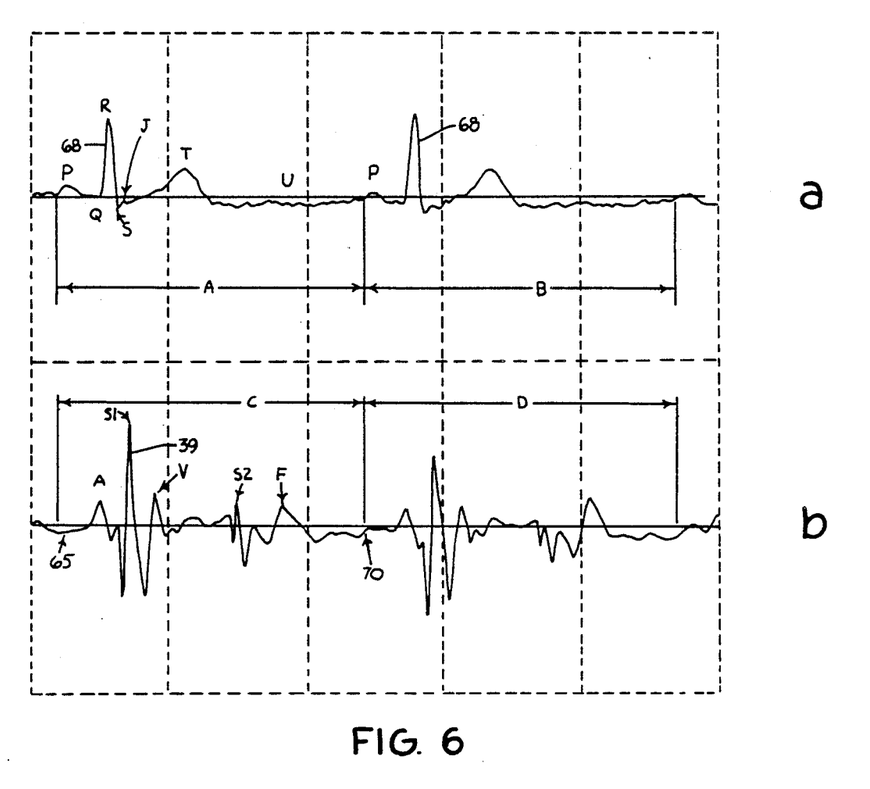
FIG. 6 shows a and b versions of waveforms representing a series of waveforms of two full cycles of function of the heart muscle with waveform "a" representing an electrocardiographic signal and waveform "b" representing a compression wave signal.

The band limited analog signal output (also referred to as an analog compressional wave signal) from low pass filter 38 is a signal which is composed of a series of repeat cycles of the function of the heart muscle of the patient. An example of a series of such cycles of the compression waves 24 picked up by the accelerometer 22 is illustrated in FIG. 6b of the drawings where individual Cycles C and D are illustrated and represent a graph of an analog compressional wave signal. The individual amplitude spikes in the signal represent muscle function of the heart and it will be noted from Cycle C and Cycle D that specific heart muscle functions are repeated. Examples of these repeat functions are illustrated by wave peak 39 of each of the Cycles C and D. Close examination of the individual cycles will reveal that in a normally functioning heart, the amplitudes of the various sections of the compression wave illustrated by the cycles in FIG. 6b are repeated cycle after cycle. In a normally functioning heart, the o individual Cycles C and D which result from the compression wave 24 generated by the heart muscle function will be constantly repeated to produce a series of such cycles which look virtually identical.

The band limited analog signal present in this series of individual cycles is fed from low pass filter 38 to an analog-to-digital converter 41. Converter 41 converts the analog signal to a digital format. Converter 41 is preferably a high-resolution, 16-bit analog-to-digital converter which transforms the analog vibration signal from low pass filter 38 to an equally spaced digital vibration signal. The output from converter 41 is a digital signal or digital compressional wave signal capable of being further analyzed but which is representative of a series of cycles of heartbeat and, therefore, representative of the compression waves 24 detected by the accelerometer 22.

At this point, the digital compressional wave signals which have undergone band pass conditioning in the low pass filter 38 are fed to a time domain analysis module 42. The time domain analysis module 42 improves the digital signal by eliminating non-representative cycles of the series of cycles. Frequently, in the detection of compression waves 24, premature heartbeats, artifacts, ambient noise and other noise signals will distort the compression wave 24 so that accelerometer 22 will pick up undesirable and extraneous noise compression waves. The signal detected by the accelerometer 22 must be improved to reduce the artifacts present in order to provide a useful signal for analysis.

The series of digital (digital compressional wave signals), signals from converter 41 are fed to the cardiac cycle interval selector 43. Selector 43 determines the cardiac cycle interval for each heartbeat. As an example, a single cycle of function of the heart muscles is represented as previously indicated by individual Cycles C and D. Refer to FIG. 6b of the drawings for this reference. Selector 43 identifies the individual cycles and eliminates those individual cycles which contain artifacts, premature beats and the like. The cycles carrying interference are non-typical signal cycles. Elimination of non-typical cycles can be accomplished as an example by comparison of the spikes 39 and other characteristics of each cycle. Those cycles which are non-characteristic or non-typical of the series of cycles are eliminated from the series of cycles. In this way, if an ambient compression wave is generated from noise within the room where the test of the patient is occurring or from compression waves transmitted to the patient's body from the table on which the patient is lying, the ambient compression wave will be eliminated by selector 43. By eliminating these non-typical cycles, the series of cycles is improved to provide a series of cycles which is typical of the patient's heart muscle function. A typical signal of the patient's heart muscle function may be a signal which indicates that the patient has muscle function impairment. Nevertheless, the signal becomes the typical signal for that patient's impairment and, consequently, may be analyzed and understood by a skilled physician upon display for observation.

Continue to refer to FIG. 3 of the drawings. Consequently, selector 43 specifically eliminates from the series of cycles those cycles which are not typical of the patient's heart muscle function. As will be explained later, spike 47 of FIG. 5b may be "typical" of an impaired muscle and would be a feature of a muscle function signal which would not be eliminated from the series of signals by selector 43. Consequently, a series of cycles containing the same indication of impairment as illustrated by spike 47 would be preserved by the selector 43 for further processing according to the present invention.

After selector 43 has selectively eliminated those single cycle sections of non-typical signal, the output of selector 43 becomes a series of individual or single cycles of the heart muscle function which are typical of the patient's heartbeat. These single cycle selections of the digital signal are then fed to signal averaging module 44 where a series of individual cycles from selector 43 are averaged. The number of individual cycles which are averaged by module 44 will be dependent upon the number of individual cycles of heartbeat which are detected by accelerometer 22. As few as two individual or single-cycle portion may be averaged. Even a single cycle may be "averaged" or selected. The desired result is to obtain a single "typical" cycle of the subject's heart beat for analysis purposes. Also, a relatively large number of such cycles may be averaged. The averaging is undertaken to generate an averaged cycle which is characteristic of the subject's heart muscle function. Essentially, averaging module 44 is designed to improve the signal characteristics to reduce the artifact present in the signal and to provide an output signal which is an averaged compressional wave signal which can be analyzed with some degree of confidence and certainty by a skilled observer of the final waveform.

Next, the averaged compressional wave signal from module 44 is directed to a frequency domain analysis module 48. The averaged compressional wave signal is directed to conditioner 49 of the frequency doman analysis module 48. Typically, the full-cycle, averaged waveform of a full cycle of the heart muscle is selected between two points where the waveform does not go to zero. This failure of the selected full cycle to go to zero constitutes a distortion in the waveform and, accordingly, there is a need to compensate for this "energy leakage" when the signal is further processed in the frequency domain analysis module 48. Conditioner 49 is used to condition the averaged compressional wave signal at the beginning and at the end of the cycle in order to remove this waveform distortion.

Figure 8:
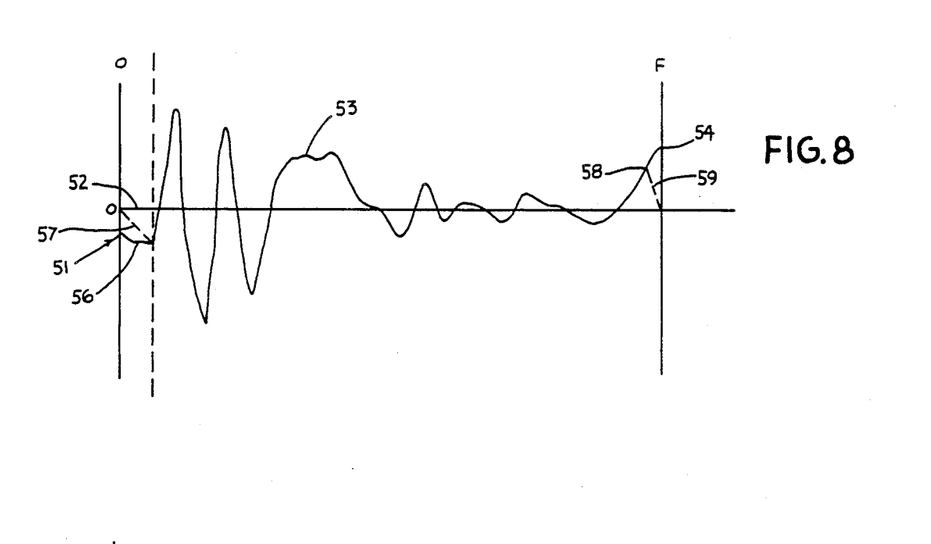
FIG. 8 is a compensated single cycle of a waveform and FIG. 9 is a graph of the energy levels at frequencies between about 0.025 Hz to about 50 Hz of the analog signal generated by heart function-generated compression waves.

FIG. 8 of the drawing is an illustration of the function of conditioner 49. A full cycle might have a beginning or zero starting point 51 which is below base line 52 which is the zero line of the waveform illustrated in the graph of waveform form 53 in FIG. 8 of the drawings. Likewise, the end of the full cycle of wave 53 may occur at a point 54 which is above zero or above base line 52. It is desirable to have the wave 53 begin at the base line or the zero line and also end at zero or the base line 52. The function of conditioner 49 is to ensure that wave 53 is compensated to begin the wave at zero and also end the waveform at base line zero.

Just as the beginning of the waveform 53 is conditioned the end distortion 58 is removed also. The waveform 53 is conditioned to provide a waveform 59 which brings the waveform 53 to zero at the end of the cycle. Thus, amplitude distortion of wave form 53 is completed.

Figure 9:
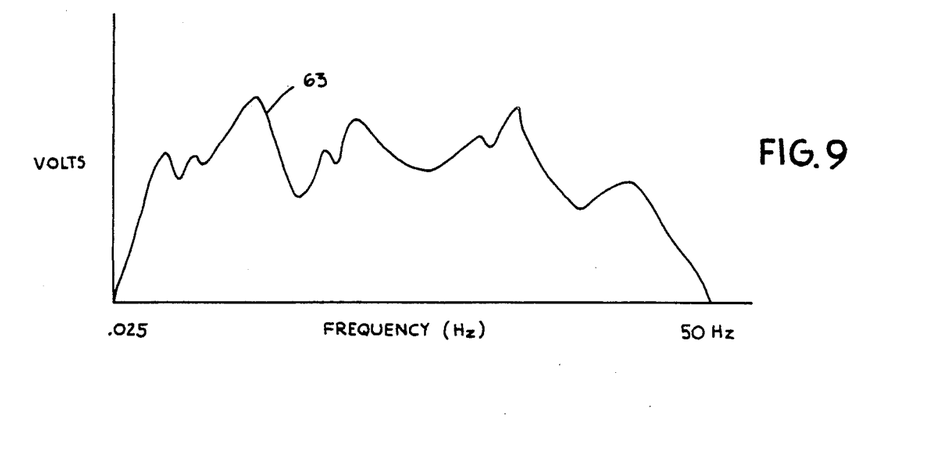

Next, the conditioned signal is analyzed by a Fourier analyzer. The Fourier analyzer 61 effectively transforms the conditioned waveform from conditioner 49 into discrete frequencies in the range from 0.025 Hz to about 50 Hz. This Fourier analysis then permits calculation of the energy at each of the discrete frequencies in the indicated range. The wave energy calculation takes place in wave energy calculator 62 where the total energy at each of the discrete frequencies is calculated. Wave envelope 63 illustrated in FIG. 9 indicates the energy levels of wave 63 at particular frequency levels from 0.025 Hz up to 50 Hz. An output 55 from wave energy calculator 62 is an output signal which is representative of the total energy of the conditioned and averaged signal.

Next, the energy output signal 55 from wave energy calculator 62 is directed to display means 63 simultaneously with an averaged compression signal 60 from signal averaging module 44. Display means 63 can be a variety of display or storage devices designed to provide a display graph for visual analysis or storage of the data on magnetic or other media. Other media may include laser devices and similar systems. For the purpose of this invention, the expression "display device" and also "recording device" encompasses all such devices and systems. The display device may be simply a data recording device or it may be a display device also incorporating a data storage feature of well known types. For instance, if the various functions set forth above constitute the results of a computer software system, the display means may be a video display means which an observer or analyst can observe to study the full cycle which is characteristic of a patient's heart muscle function. A typical example of a display means 63 might be a video monitor. For the purpose of illustration, this waveform might appear the same as the signal illustrated in FIG. 5b of the drawings. Another alternative for display means 63 might be a graph display means which would create a printed record of the waveform for visual analysis and for archiving. A typical such graph is the kind used in connection with an electrocardiogram. Computer tape or disk storage are other examples of display means. Any of these display means can be effectively used by the present invention. The display means may also involve a visual display device such as a graph or the type of record commonly used with seismographic or electrocardiographic devices.

Figure 5A:
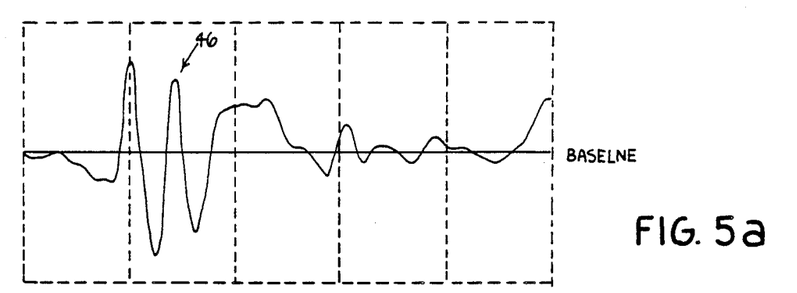
FIG. 5a is a compression waveform of a normal human heart muscle function measured by the apparatus and method of the present invention.
Figure 5B:
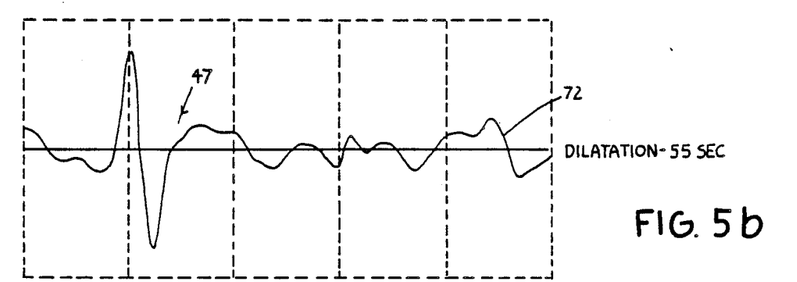
FIG. 5b is a compression waveform of the muscle function of the same human heart measured by the present invention illustrating a transient abnormality in the heart function induced by obstruction of blood flow in one of the coronary arteries.

A more complete understanding of the function of the invention and process will be apparent with an explanation of how the present invention provides a skilled analyst with the ability to identify abnormal function of muscles of the human heart. Refer first to FIGS. 5a and 5b of the drawings. FIG. 5a of the drawings is a single cycle of a patient's heartbeat. In this case, the cycle is that of a 64-year-old male patient. This graph represents a full cycle of the patient's heart muscle from beginning to a repeat cycle. This graph was generated with the blood flow to the heart muscles sufficient to supply blood to the patient's heart muscle. This particular patient had diseased arteries with localized narrowing of the diseased arteries so that blood flow to the heart muscle was somewhat constricted. Nevertheless, for this particular patient, the wave pattern illustrated by FIG. 5a of the drawings did represent the normal wave pattern for that particular patient. In other words, the patient's heart was generating compression waves which, when measured by the method and apparatus of the present invention, generated a cycle of compression waves represented by FIG. 5a of the drawings.

FIG. 5b is another cycle of the same 64-year-old male patient's heart muscle function as measured by the device and method of the present invention, but in this particular case, the patient was undergoing a procedure to dilate a localized area of narrowing in a diseased artery. This process involved an angioplasty procedure in which a balloon is inserted into the diseased artery and is inflated in the section of the artery where the artery is narrowed by localized fatty deposits. The balloon was then inflated in this procedure so that the narrowed area is dilated to then increase the blood flow through the artery to the patient's heart muscle. During the process of inflating the balloon in order to dilate the artery, blood flow through the artery is restricted or stopped entirely. The compression wave pattern generated by the patient's heart muscle at the time that the angioplasty procedure was occurring changed in response to stopped blood flow fan 55 seconds momentarily in the artery and, thus altered the compression waves generated by the temporarily ischemic heart muscle as is illustrated by FIG. 5b of the drawings.

A comparison of the wave pattern generated by the same patient during a normal, for that patient, heart function cycle and for a cycle during the angioplasty procedure will reveal the ability of the present invention to detect conditions where arteries are not properly supplying blood to heart muscle. Attention is specifically directed to spike 46 of FIG. 5a of the drawings. Spike 46 is a typical spike present in this particular patient's normal heart function. Generation of this spike 46 occurs as a result of heart muscle function which produces the indicated compression waves 24. Next, reference to FIG. 5b of the drawings will reveal that spike 46 no longer exists in the wave pattern but is replaced by a spike 47 which is dramatically different from spike 46. Spike 47 occurred as described when the balloon restricted and terminated blood flow in the artery.

A skilled analyst would recognize that spike 47 is not characteristic of a properly functioning heart muscle and would immediately recognize that there is impairment of heart muscle function. This impairment would typically be due to restricted blood flow. The impairment of the muscle function is caused by the reduced or eliminated supply of oxygen to the particular afflicted heart muscle as a result of constriction in the artery supplying that particular muscle.

It will be apparent from this illustration that analyzing a wave pattern detected according to the present invention will reveal to a skilled analyst that impaired heart muscle function is occurring in a patient.

The final display means 63 is desired in order to visually display a graph which might appear like that illustrated in FIGS. 5a and 5b of the drawings for the purpose of analysis. In the case where an archived graph might be utilized, a patient such as the 64-year-old patient might have an archived heart pattern which is for the purposes of illustration similar to FIG. 5a of the drawings. With this as a reference of the patient's "normal heart muscle function," a subsequent test of the patient's heart muscle function might create a graph illustrated by FIG. 5b of the drawings. A skilled analyst would easily recognize that the waveform 72 in FIG. 5b has changed from the previous characteristic or normal wave pattern and would, therefore, immediately recognize that impairment of the patient's heart muscle function has occurred and is affecting the proper functioning of the heart. In this way, the compression waves 24 which are characteristic of the function of the heart muscles are displayed on a display means for analysis to provide noninvasive method of screening patients for proper heart muscle function.

Figure 4:
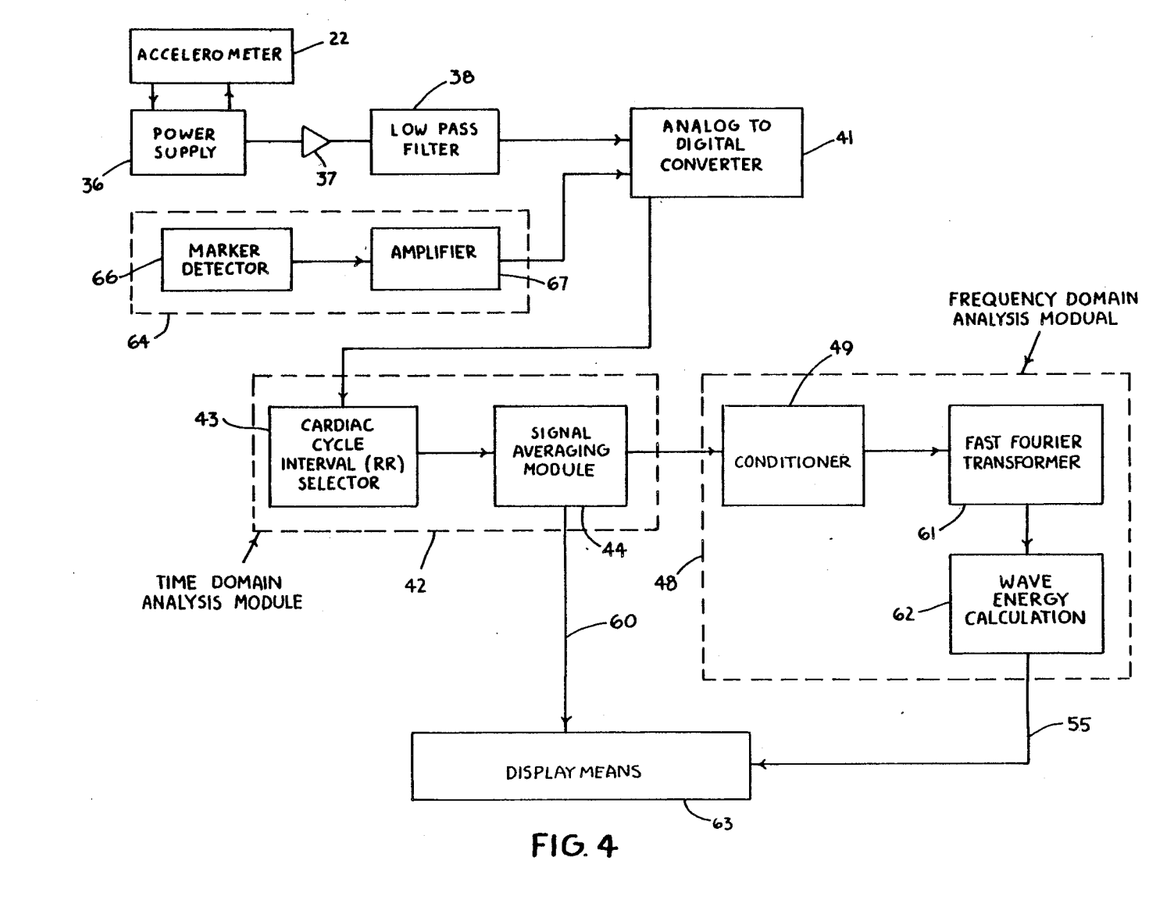
FIG. 4 is a block diagram illustrating an alternative embodiment of the invention employing a marker method and apparatus.

An alternative version of the present invention employs a marker module. Refer now to FIG. 4 of the drawings where a marker module 64 is illustrated. The function of marker module 64 is to provide a heart function reference which can be compared to the compression wave signal which is also being simultaneously generated by the heart. Preferably, marker module 64 detects heart muscle function utilizing detection characteristics which are different from the compression waves detected by the present invention. Further, module 64 should provide a reference function of the heart which is well known to physicians and others who are skilled in analyzing heart function. Known characteristics of the output of module 64 can be compared with the simultaneous detection of heart muscle function through the detection of compression waves 24 generated by the heart. A well known and well understood device for use as module 64 would be an electrocardiogram. The medical profession understands the significance of the wave forms produced by the electrocardiographic techniques. The electrocardiographic techniques (ECG) rely on the detection of the electrical field activity around the heart. The changes in this electrical field results from depolarization and repolarization of heart muscle cells which are readily measurable electrical phenomena. This electrical activity is the basis for ECG techniques. The ECG analog waveform associated with this electrical activity of the heart includes a number of medically significant segments which are currently well known by the medical profession. Experience with these measured phenomena permits an understanding of the function of the heart. The typical ECG analog waveform segments are sufficiently understood that physicians know what particular physical function is occurring in the heart. These particular functions have been identified and can be represented as a particular segment of the ECG analog waveform. It is known, for example, that in a normal "at rest" heartbeat, there first occurs a "P wave." Refer to FIG. 6B of the drawings for reference to this indication of the wave segment which involves the "P wave". This P wave comprises a small rise and drop in the analog signal amplitude. This P wave is representative of the depolarization of the atria and is immediately followed by a generally low-level signal portion which terminates in a large change in signal amplitude. If the initial change is negative, it is referred to as the Q wave. The portion of the ECG analog waveform between the end of the P wave and the beginning of the Q wave is called the PQ (or PR) interval or PQ (or PR) segment. Physiologically, this interval represents a pause in the heart sequence.

Following the Q wave phenomenon, there may be a rapid increase in the signal voltage to a maximum amplitude. This maximum amplitude is represented on the waveform in FIG. 6A of the drawings by the sharp spike in the waveform and is commonly referred to as the R wave. After the maximum amplitude occurs, there may be a sharp drop in amplitude to below the level of the PQ interval. This is followed by a rise back to the PQ interval level and is characterized and referred to as the S wave. The S wave is then normally followed first by a level segment in the waveform which terminates in a further rise and fall in amplitude known as the T wave. The point where the S wave terminates in the beginning of the level segment is known as the J point. And the level section or essentially level section between the end of the S wave and the start of the T wave is known as the ST segment. The Q, R, and S waves are referred to the QRS complex and represent ventricular depolarization. The T wave represents repolariZation of the ventricles. After the T wave phenomenon there is a brief additional level segment of the wave before the commencement of the P wave of the next heartbeat. Thus it will be apparent that the ECG signal provides a method of identifying a complete cycle of the function of the heart which is well known and understood by practitioners of medicine.

The electrical depolarization of the heart muscle cell membranes stimulates the contractile elements within the cells to shorten, resulting in the mechanical contraction of the heart muscle. Thus, the P wave represents atrial depolarization and leads to atrial contraction. The atria pump blood into the ventricles and produce a contraction wave detected by the seismocardiograph during this process, labeled as "A" wave in FIG. 6b. The QRS wave represents the electrical depolarization of the ventricles and leads to their contraction. At the very onset of ventricular contraction, valves between the atria and ventricles are forced closed by the rising pressure in the ventricles, thus preventing backwash of blood from the ventricles to the atria. This valve closure produces an audible sound, commonly called the first heart sound or S1. There is a low frequency wave produced at valve closure which is labeled "S1" in FIG. 6b. Immediately after S1, ventricular contraction produces a compression wave labeled as the "V" wave in FIG. 6b . After the ventricles force blood forward into the aorta and pulmonary artery, and begin to relax, pressure in the aorta and pulmonary artery close the valves between the ventricles and these arteries to prevent backwash of blood. This valve closure produces an audible sound, commonly called the second heart sound, or S2. There is a low frequency wave at this point labeled "S2" in FIG. 6b. Finally, there is passive filling of the ventricles from the atria, prior to the next atrial contraction. This passive filling of the ventricles produces a compression wave labeled "F" in FIG. 6b.

Since each change in the electrical phenomena surrounding the function of the heart is so well known, and is often used by physicians to detect the function of a patient's heart, this known and well understood information and activity can also be employed by the present invention as a marker reference for the purpose of comparison to corresponding compression waves generated by heart muscle function.

Because of the well understood characteristics of the ECG signal, physicians can identify impairment of heart muscle function by variations from normal in the ECG signal. Consequently, the ECG signal can be used as an effective marker for comparison to compression waves generated by the heart muscle function. As an example, the QRS wave section of the ECG signal can be identified and just slightly precede the ventricular muscle contraction which is generating compression waves and which are detectable using the method and apparatus of the present invention. Consequently, physicians can use such a marker reference in order to compare the periodic function of various heart operations to the expected muscle activity which results from detection of musclegenerated compression waves.

If variations occur in the ECG signal, these variations could have corresponding variations in the heart muscle function and accordingly accompanying variations in the compression waves generated by the heart muscle. Therefore, the ECG technology provides an effective method of marking the heart muscle function with the corresponding compression wave generation. For this reason, a preferred embodiment of this invention utilizes an electrocardiogram as the marker module 64. In this version of the invention, the marker module 64 is an ECG system which contains a marker detector 66. Marker detector is simply the ECG apparatus which detects the electrical activity of the heart and generates the well recognized ECG signal illustrated in FIG. 6A of the drawings.

This detected electrical activity is an analog signal which is directed to an amplifier 67 for amplification. This analog marker signal is then directed to the analog to digital converter 41 along with the band limited analog signal from filter 38. In effect, the analog signal from amplifier 67 and the band limited analog signal from 38 are signals which represent activity of the heart measured by using two different detection techniques. In the case of the accelerometer 22 a compression wave created by the function of the heart muscle is detected. Simultaneously, the marker detector is detecting the electrical field activity around the heart so that both signals arrive at analog-to-digital converter 41 on the same time scale for conversion to a digital signal. Since both the band limited analog signal and the analog marker from amplifier 67 are on the same time scale, the output signal from analog to digital converter signal will ultimately produce a graphic display which is essentially the same as that illustrated by FIGS. 6A and B of the drawings. In this display, the ECG signal illustrated by FIG. 6A of the drawings is recorded on the same time line as the compression waVe signal representation illustrated as FIG. 6B.

Since both of the signals are on the same time line, the full heart muscle function cycles of the heart can be readily identified. First, the full-cycle function of the heart is readily identified from the ECG signal and in FIG. 6A of the drawings is illustrated by cycles A and B. The full-cycle function of the heart has been chosen to start with the beginning of the P wave and terminating at the following beginning of an additional P wave function. The corresponding compression wave cycle is referred to as cycle C which begin at point 65 and terminates at point 70 in FIG. 6B of the drawing. Thus it will be apparent that by use of a marker module, every corresponding point or function of the ECG signal can be compared on a time scale with the compression wave signal for exactly the same cycle. Any unusual occurrence in the ECG signal can be readily compared to the corresponding portion of the compression wave cycle so that physicians can readily identify the abnormality occurring in the heart as one which is affecting heart wall muscle function.

Figure 7:
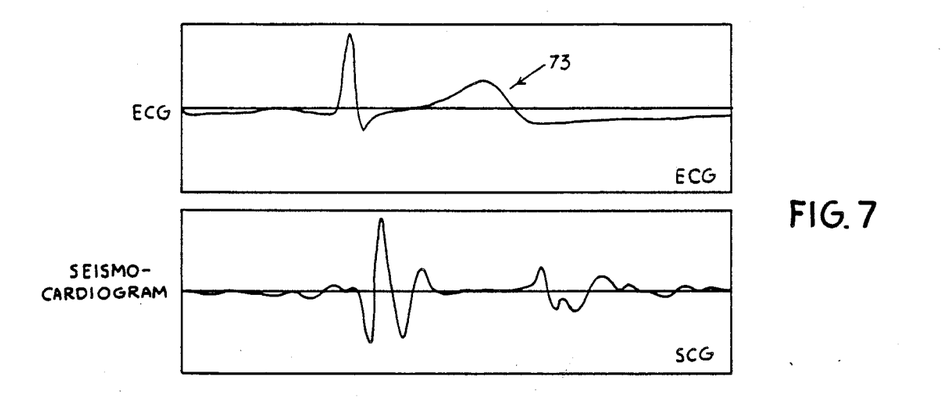
FIG. 7 is an averaged wave of a single cycle of heart function.

After the analog marker signal is input to the analog to digital converter 41, the output from converter 41 then becomes a combination of the marker signal and the compression wave signal. From that point on, the selection by selector 43, signal averaging in averaging module 44 and analysis in the frequency domain analysis module 48 is exactly the same as that described hereinbefore. The marker signal does not enter the frequency domain analysis module 48. The only change which occurs is that of the output signal or average compression signal 60 now contains a marker detector signal component 73. The resulting display by the display device 63 would carry two display signals as identified in FIG. 7 of the drawings.

Thus it will be apparent that the present apparatus provides an effective and useful method for noninvasive detection of abnormalities in the function of the muscle of the heart wall. This detection method utilizes the generation of compression waves from the heart wall muscle function as previously noted to identify the characteristics of that muscle function. As previously indicated, the first procedure is to detect compression waves which are travelling through the body tissue from the heart to the outside surface of the body. Detecting these compression waves can take place by the use of an accelerometer 22 which has a usable response to compression waves and detects compression waves beginning at a frequency of approximately 0.025 Hz.

An analog signal is generated which is essentially an analog compressional wave signal representing the compression wave. Next, the detected compression wave is frequency limited so that only those frequencies from the compression wave which fall in the range of 0.025 up to about 50 Hz are identified. This results in a band limited signal.

Next, the analog band limited signal is converted to a digital compressional wave signal representing a series of cycles of heartbeat of the patient. The original compression wave signals which are detected are a series of cycles of compression wave signals representing repetitions of the heart function. These repeated cycles of the heart muscle function are thus converted to a digital signal. Next, in order to eliminate ambient noise, as previously indicated and also to eliminate spurious signals, selected single-cycle portions of the digital compression wave are selected. These selected single-cycle portions are those single cycles which are characteristic of the patient's heart function for a full single-cycle. These are the "typical" cycles of the heart function which will ultimately be analyzed by the physician. The typical cycle may not be a normal cycle. A typical cycle may contain an indication of heart muscle malfunction. However this typical cycle is typical of the malfunctioning heart. This would be different from normal function of the heart muscle which implies proper function of the heart muscle. A number of the selected single-cycle typical cycles of the heart function may then be averaged. The number of typical single-cycle portions which are averaged will depend upon the number of single cycle functions that have been detected. The averaged typical cycles may contain as few as two typical cycles with no limit on the final number which may be chosen for averaging. The averaging step occurs in order to produce a final single-cycle function of the heart which is then displayed for analysis.

After the typical single cycles are averaged, that resulting signal is conditioned to remove waveform amplitude distortion from the average compression signal. The waveform is conditioned as previously indicated in order to remove distortion from the beginning and the end of the full single-cycle waveform so that further analysis o of the waveform can occur.

Next, the conditioned signal is analyzed in discrete frequency components, after which the total energy level of each of the discrete frequency components is calculated to provide an energy level output signal. Finally, the unprocessed or the analyzed and averaged signals are displayed on a display device for review by a physician or analyst who is skilled in analyzing waveforms which characterize the function of the heart. The display device may vary according to the needs of the analyst and the need for archiving the data. A simple display device might include a cathode ray tube display for immediate analysis. A more permanent record may be needed and is often desired for future reference. A photographic record of the cathode ray tube display might be made. Further, a stylus graph recorder or other printout device using state of the art techniques can also be coupled to the output circuits to provide a tracing of the selected heart activity and thereby provide a permanent record such as a computer magnetic media in the same way that a permanent record is produced when using an electrocardiogram.

Graphic display is frequently useful since noninvasive testing of muscle heart function is often desirable when a patient is not suspected of having cardiovascular disease so that the normal and healthy pattern of the heart muscle function can be used as a reference for any future impairment which may occur. By having a normal and healthy reference, the physician can compare the normal graph to a later graph which may indicate heart disease. By making such a comparison, the physician is better able to identify the extent and nature of the heart disease experienced by the patient.

The above method also can be enhanced by utilizing a marker signal. As indicated earlier in connection with the use of an ECG system as a marker signal, the process may be altered to include a simultaneous detection of the electrical activity about the heart at the same time that the compression wave function of the heart is being detected. This simultaneous detection of electrical activity of the heart permits the electrical activity to be used as a reference signal for assistance in analyzing the nature of the compression wave signal which is also generated. In this method, the detected electrical activity is converted to an analog marker signal representative of this activity. This analog marker signal is also converted to a digital signal for comparison with the compression wave signal.

Thus it will be apparent that the invention brings to the medical art an instrumentation and method for noninvasively measuring the activity of the heart muscle. This noninvasive method of detecting heart function provides a quick and convenient way of monitoring heart activity without risking complications on the part of the patient and further provides a very cost-effective method of quickly checking a patient's heart function. By using this system, a practicing physician can perform in-depth analysis of a patient's heart function in his office without the requirement for extensive long-term preparation of the patient prior to undertaking the examination.

It will be apparent also from the foregoing description of the apparatus and method according to the present invention that a number of variations may be incorporated in the apparatus and method without departing from the spirit and scope thereof. For example, the marker module might be instrumentation which picks up the magnetic activity around the heart rather than electrical field activity. Such devices and methods are contemplated by the present invention. Further, the particular configuration of the various components of the accelerometer 22 can be varied within the scope of the invention. Further, various electrical apparatus and computer software programs may be utilized for the various signal altering functions identified in FIGS. 3 and 4. All of these variations can be made without departing from the spirit and scope of the invention which has, as its central concept, the use of compression waves generated by heart muscle function for detection of proper function of those heart muscles.

What is claimed is:

1. Apparatus for the diagnostic display of motion signals characterizing the ventricular wall motion of a patient's heart comprising:

compression wave detector means, coupled to said patient, responsive to cardiac induced compression waves at the surface of said patient, for generating motion signals indicative of said compression waves;

cardiac cycle selector means coupled to said patient for selecting normally conducted sinus beats of said patient's heart and for generating a cardiac cycle signal during each of said normally conducted beats;

display means coupled to said cardiac cycle selector means and coupled to said detector means for diagnostic display of averaged data corresponding to said motion signals collected during said cardiac cycle signals.

2. The apparatus of claim 1 wherein said compression wave detector means comprises:

an accelerometer having a sensitivity of one microinch at one hertz.

3. The apparatus of claim 1 wherein said compression wave detector means comprises:

an accelerometer having a linear frequency response from 0.025 hertz to 800 hertz.

4. The apparatus of claim 1 wherein said cardiac cycle selector means comprises:

electrocardiographic detection means for determining the R-R intervals of patient heartbeats and for establishing a normal range of R-R intervals for said patients heart;

R wave to R wave interval selection means coupled to said electrocardiographic detection means for selecting beats of said patients heart within said normal range of R-R intervals and for generating a cardiac cycle signal indicating the occurrence of a normally conducted sinus beat of said patients heart.

* * * * *

UNITED STATES PATENT AND TRADEMARK OFFICE
CERTIFICATE OF CORRECTION

PATENT NO. : 4,989,611  
DATED : February 5, 1991  
INVENTOR(S) : Zanetti, et al.

It is certified that error appears in the above-identified patent and that said Letters Patent is hereby corrected as shown below:

Title page:

In "OTHER PUBLICATIONS", line 14, change "PCT" to --PCB--.

Col. 1, line 45, delete "of" after the word "use".

Col. 2, line 30, change "201testing" to --201 testing--.

Col. 3, line 1, delete "o" after the word "the".

Col. 4, line 49, change "0.25 Hz" to --0.025 Hz--.

Col. 5, lines 12 & 13, change "seismocardiography R" to --seismocardiograph --.

Col. 5, line 13, change "R" to --TM-- after "seismocardiograph".

Col. 5, line 22, change "Piezio-tronic" to --Piezo-tronic--.

Col. 7, lines 6 & 7, delete "," after the word "human".

Col. 7, line 65, change "fluoride" to --flouride--.

Col. 8, line 19, change "2" to --21--.

Col. 9, line 54, delete "o" after the word "the".

UNITED STATES PATENT AND TRADEMARK OFFICE
CERTIFICATE OF CORRECTION

PATENT NO. : 4,989,611

DATED : February 5, 1991

INVENTOR(S) : Zanetti, et al.

It is certified that error appears in the above-identified patent and that said Letters Patent is hereby corrected as shown below:

Col. 13, line 1, after the word "to", insert --the balloon being inflated. The inflated balloon--.

Col. 13, line 1, change "fan" to --for--.

Col. 13, line 1, delete "momentarily" after the words "55 seconds"

Col. 13, line 2, delete "," after the word "and".

Col. 14, line 59, change "repolariZation" to --repolarization--.

Col. 15, line 50, change "musclegenerated" to --muscle generated--.

Col. 16, line 19, change "WaVe" to --wave--.

Col. 17, lines 28 & 29, change singlecycle" to --single-cycle--.

Col. 17, line 32, change "single cycle" to --single-cycle--.

Col. 17, line 38, change "single cycles" to --single-cycles--.

Col. 20, line 8, change "patients" to --patient's--.

Col. 20, lines 11 and 14, change "patients" to --patient's--.

UNITED STATES PATENT AND TRADEMARK OFFICE
CERTIFICATE OF CORRECTION

PATENT NO. : 4,989,611

DATED : February 5, 1991

INVENTOR(S) : John M. Zanetti, et al.

It is certified that error appears in the above-identified patent and that said Letters Patent is hereby corrected as shown below:

Column 11, line 19, change "doman" to --domain--.

Signed and Sealed this

Thirteenth Day of April, 1993

*Attest:*

STEPHEN G. KUNIN

*Attesting Officer*    *Acting Commissioner of Patents and Trademarks*